US00PP26887P2

(12) United States Plant Patent
Ui et al.

(10) Patent No.: US PP26,887 P2
(45) Date of Patent: Jun. 28, 2016

(54) ***PETUNIA* PLANT NAMED 'SAKPET095'**

(50) Latin Name: *Petunia hybrida*
Varietal Denomination: SAKPET095

(71) Applicant: Sakata Seed Corporation, Tsuzuki-Ku, Yokohama (JP)

(72) Inventors: Akinobu Ui, Iwata (JP); Randy Holbert, Salinas, CA (US)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/544,470

(22) Filed: Jan. 7, 2015

(51) Int. Cl.
*A01H 5/02* (2006.01)

(52) U.S. Cl.
USPC ..... Plt./356.13

(58) Field of Classification Search
USPC ..... Plt./263.1, 356.13
See application file for complete search history.

(56) References Cited

PUBLICATIONS

Sakata Ornamentals website (http://www.sakataornamentals.com/index.cfm/fuseaction/mobile.plant/plantID/3643/jsessionID/8F5428A6E22A3ABE124F8273F8DA0B02.railo-04/index.htm). Nov. 23, 2015 (1 page).*
PLUTO: Plant Variety Database, Nov. 21, 2015, citation for 'SAKPET095' (1 page).*

* cited by examiner

*Primary Examiner* — Susan McCormick Ewoldt
*Assistant Examiner* — Karen Redden
(74) *Attorney, Agent, or Firm* — Bethany R. Roahrig; Cochran Freund & Young, LLC

(57) ABSTRACT

A *petunia* plant particularly distinguished by having a violet and white start-shaped flower color and a mounding plant growth habit, is disclosed.

2 Drawing Sheets

Genus and species: *Petunia hybrida.*
Variety denomination: 'SAKPET095'.

BACKGROUND OF THE NEW PLANT

The present invention comprises a new and distinct variety of *petunia* plant, botanically known as *Petunia hybrida*, and referred to by the variety name 'SAKPET095' and characterized by having a violet and white star-patterned bicolored flowers with a mounding plant habit. *Petunia* variety 'SAKPET095' originated from a hybridization in Kakegawa, Japan in 2010. The female parent was a proprietary *petunia* breeding line named 'SRV-1' (unpatented) having a blue flower with a semi-creeping plant habit. The male parent was a proprietary *petunia* breeding line named '9BR-51a' (unpatented) having a blue and white star-patterned bicolored flowers and a mounding plant habit.

In June 2010, 'SRV-1' and '9BR-51a' were crossed and 1,000 seeds were obtained. In November 2010, the $F_1$ seed was sown in the greenhouse, cultivated and plant lines were produced with flower colors of blue, violet and white star pattern and mounding and semi-creeping plant habit. In March 2011, a plant line was selected within the $F_1$ plants that had violet star flowers and a mounding plant growth habits. The selection was named 'L2011-462'.

From February through March of 2011, 'L2011-462' was evaluated for day length neutral flowering response. In March 2011, 'L2011-462' was first vegetatively propagated, cultivated, and transplanted to the field for outdoor evaluation. In October 2011, the breeder confirmed that line 'L2011-462' was fixed and stable. In January 2012, the breeder confirmed the line to be fixed and stable. 'L2011-462; was subsequently named 'SAKPET095' and its unique characteristics were found to reproduce true to type in successive generations of asexual propagation via vegetative cuttings in Salinas, Calif.

SUMMARY

The following are the most outstanding and distinguishing characteristics of this new variety when grown under normal horticultural practices in Salinas, Calif.

1. Violet and white star-patterned flowers; and
2. A mounding plant habit.

DESCRIPTION OF THE PHOTOGRAPHS

This *Petunia* plant is illustrated by the accompanying photographs which show the plant's overall plant habit including form, foliage, and flowers. The photographs are of a one and a half year old plant grown in Salinas, Calif. under greenhouse conditions in the spring. Plants were stuck in November 2013 and transplanted into 4 inch pots in December 2013 and 12 inch pots in January 2014. The colors shown are as true as can be reasonably obtained by conventional photographic procedures.

DESCRIPTION OF THE NEW VARIETY

Figure 1:
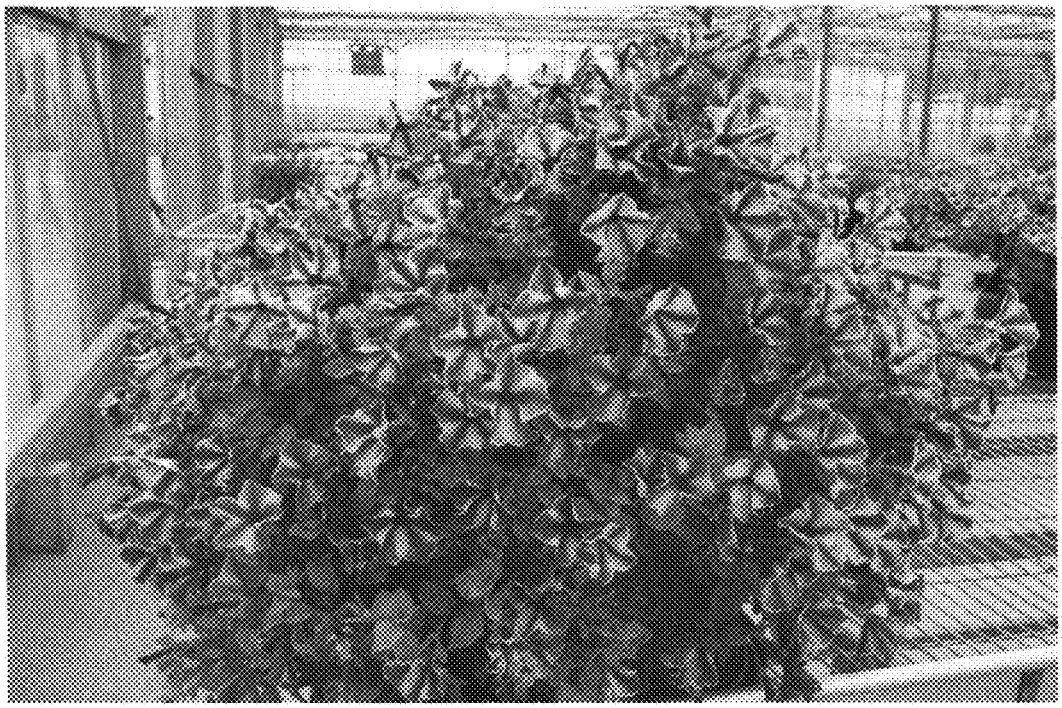
FIG. 1 shows the overall plant habit of the plant grown in a pot.
Figure 2:
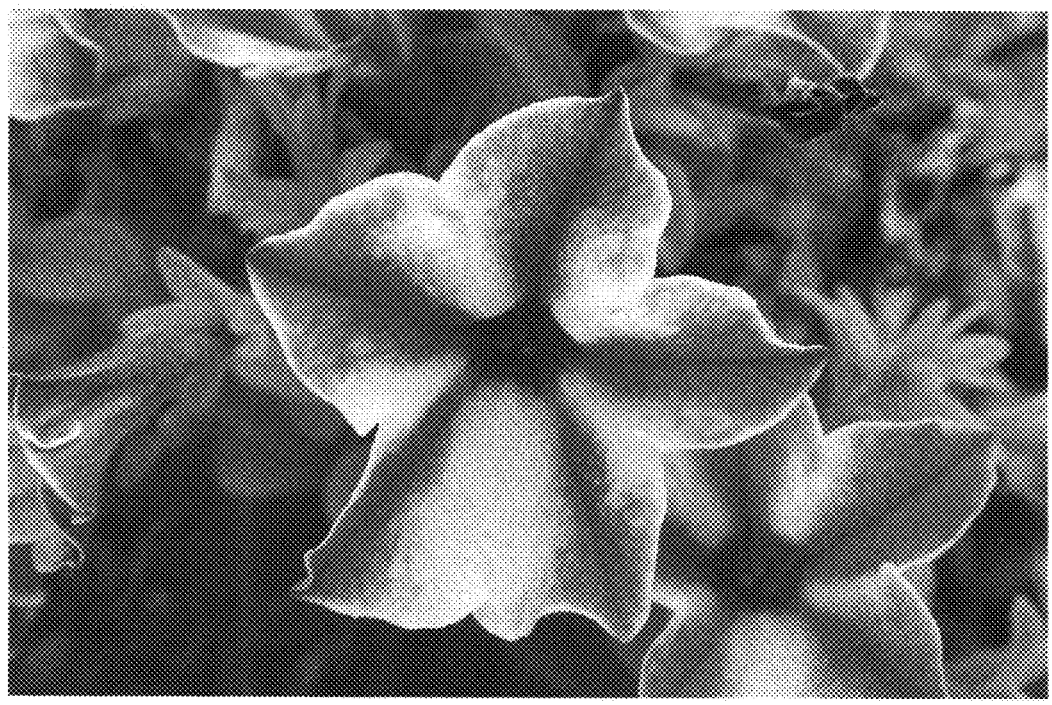
FIG. 2 shows a close-up of the mature inflorescence of the plant.

The following detailed descriptions set forth the distinctive characteristics of 'SAKPET095'. Data was collected on one and a half year old plants transplanted into 12-inch pots from rooted cuttings in Salinas, Calif., under greenhouse conditions in the spring 2014. Plants were pinched once during growth. Color references are to The Royal Horticultural Society of London color chart (R.H.S.), 4th edition (2001). Anatomic labels are from *The Cambridge Illustrated Glossary of Botanical Terms,* by M. Hickey and C. King, Cambridge University Press.

Classification:

*Family*.—Solanaceae.

*Botanical.—Petunia hybrida.*

*Common.—Petunia.*

*Designation*.—'SAKPET095'.

Parentage:

*Female parent*.—Proprietary *petunia* line 'SRV-1' (unpatented).

*Male parent*.—Proprietary *petunia* line '9BR-51a' (unpatented).

Growth:

*Time to produce a rooted cutting*.—About 4 weeks.

*Environmental conditions for plant growth*.—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Habit and form*.—Mounding, trailing and freely branching.

*Height*.—About 24.0 cm from soil line to top of foliage.

*Spread*.—About 80.0 cm.

*Number of branches*.—About 8 main basal branches; many secondary and tertiary branches.

*Length of branches*.—40.0 cm to 45.0 cm.

*Diameter of branches*.—3.0 mm.

*Life cycle*.—Annual; a tender perennial in warm climates.

*Time to bloom from propagation*.—6 to 8 weeks.

*Flowering requirements* (*season*).—Will flower so long as temperature is above 13° C. and greater than 12 hours of daylight.

*Temperature tolerances*.—No particular temperature tolerances observed.

Stems:

*Stem color*.—RHS 144A (Yellow-Green).

*Anthocyanin color*.—None.

*Stem pubescence*.—Heavy.

*Stem pubescence color*.—RHS N155A (White).

*Stem description*.—Pliable; circular cross-section.

*Stem length*.—About 28.0 cm total.

*Stem diameter*.—About 2.0 mm.

*Internode length*.—About 2.0 cm.

Leaves:

*Leaf arrangement*.—Alternate.

*Leaf shape*.—Ovate.

*Leaf apex*.—Obtuse.

*Leaf base*.—Attenuate.

*Leaf attachment*.—Sessile.

*Leaf margin*.—Entire.

*Leaf surface*.—Dull, waxy and sticky with slight pubescence. Pubescence color is RHS N155A (White).

*Venation*.—Pinnate.

*Leaf length*.—3.0 cm.

*Leaf width*.—2.5 cm.

*Leaf color*.—Upper: RHS 137A (Green). Lower: RHS 137C (Green).

*Leaf variegation*.—Absent.

*Leaf fragrance*.—Absent.

*Leaf surface pubescence*.—Slight.

*Leaf surface pubescence color*.—RHS N155A (white).

*Venation*.—Pinnate. Color: Upper surface: RHS 144A (Yellow-Green). Lower surface: RHS 144A (Yellow-Green).

Inflorescence:

*Number of flowers per node*.—1.

*Inflorescence type*.—Soliltary.

*Fragrance*.—Absent.

*Flower depth*.—2.0 cm.

*Flower diameter*.—5.5 cm.

Corolla:

*Corolla shape*.—Funnel-shaped with five fused petals.

*Corolla diameter*.—7.0 mm.

*Corolla depth*.—0.5 cm.

*Corolla tube length*.—2.0 cm.

*Corolla tube diameter*.—1.0 cm.

*Corolla tube pubescence*.—Outer surface: Heavy. Inner surface: Smooth.

*Corolla tube pubescence color*.—RHS N155A (white).

*Corolla tube color, inner surface*.—RHS 83A (Violet) with RHS N77A (Purple) veins.

*Corolla tube color, outer surface*.—Closest to RHS 83C (Violet) with RHS N77C (Purple) veins.

*Petals*.—Petal pubescence: Moderate. Pubescence color is RHS N155A (White). Petal length: 3.0 cm. Petal width: 2.5 cm. Petal shape: Obcordate. Petal apex: Acuminate. Petal margin: Entire. Petal color: Upper surface: RHS 86A (Violet) and RHS N155A (White). Lower surface: RHS 86C (Violet) and RHS N155A (White).

Calyx:

*Sepal number and form*.—5, free.

*Sepal attachment*.—Sessile.

*Sepal apex*.—Obtuse.

*Sepal base*.—Attenuate.

*Sepal margin*.—Entire.

*Sepal length*.—2.2 cm.

*Sepal width*.—5.0 mm.

*Sepal texture*.—Smooth.

*Sepal color*.—Upper surface: RHS 143A (Green). Lower surface: RHS 143C (Green).

Bud:

*Bud surface*.—Dull, sticky, moderately pubescent; pubescence color is RHS N155A (White).

*Bud length*.—3.7 cm.

*Bud diameter*.—6.0 mm.

*Bud shape*.—Cylindrical.

*Bud color*.—RHS N77A (Violet) at center and RHS N77B (Purple) at base with RHS 86A (Violet) at tip.

Peduncle:

*Peduncle length*.—4.0 cm.

*Peduncle diameter*.—1.0 mm.

*Peduncle color*.—RHS 143A (Green) with slight anthocyanin. Anthocyanin color is RHS N77A (Purple).

Reproductive organs:

*Stamens*.—Stamen form: Arranged adjacent to pistil. Stamen number: 5, free. Stamen length: 1.0 cm. Filament color: RHS 157A (Green-White) and RHS N77B (Purple) at tip. Anther color: RHS 94A (Violet-Blue).

*Pistil*.—Pistil number: 1. Pistil length: 2.0 cm. Stigma color: Slightly darker than RHS 143A (Green). Stigma length: 2.0 mm. Style color: RHS 145A (Yellow-Green). Style length: 1.9 cm.

*Ovary*.—Ovary arrangement: Superior. Ovary surface color: RHS 144A (Yellow-Green). Pollen color: RHS 97A (Violet-Blue). Pollen description: Powdery; abundant.

*Seed production*.—Absent.

Disease and insect resistance: No particular resistance or susceptibility observed.

COMPARISON WITH PARENTAL LINES AND KNOWN VARIETY

'SAKPET095' is a new and unique variety of *petunia* owing to its violet and white star-patterned bicolored flowers and mounding plant habit. 'SAKPET095' is most similar to the commercial *Petunia* variety 'Balspunurst' (U.S. Plant Pat. No. 24,369); however, there are differences as listed in the table below:

TABLE 1

Comparison with Similar Variety

| Characteristic | 'SAKPET095' | 'Balspunurst' |
|---|---|---|
| Petal color, upper surface | RHS 86A (Violet) and RHS N155A (White) | RHS 79A (Violet) with RHS N155D (White) |
| Petal color, lower surface | RHS 86C (Violet) and RHS N155A (White) | RHS 79C (Violet) with RHS N155D (White) |
| Flower diameter | 5.5 cm | 6.5 cm |
| Plant growth habit | Mounding | Compact, upright-mounded |

'SAKPET095' differs from the parental lines 'SRV-1' (unpatented) and '9BR-51a' (unpatented) as described in Table 2 below.

TABLE 2

Comparison with Parental Lines

| Characteristic | 'SAKPET095' | 'SRV-1' | '9BR-51a' |
|---|---|---|---|
| Flower color | Violet and White | Blue | Blue and white star patterned bicolor |
| Plant growth habit | Mounding | Semi-creeping | mounding |

We claim:

1. A new and distinct variety of *petunia* plant named 'SAKPET095' as described and illustrated herein.

* * * * *